United States Patent
Yang et al.

(10) Patent No.: US 8,975,436 B2
(45) Date of Patent: Mar. 10, 2015

(54) FLUORINATED ARYLENE-CONTAINING COMPOUNDS, METHODS, AND POLYMERS PREPARED THEREFROM

(75) Inventors: Yu Yang, Eden Prairie, MN (US); George G. I. Moore, Afton, MN (US); John C. Clark, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 239 days.

(21) Appl. No.: 13/508,080

(22) PCT Filed: Dec. 17, 2010

(86) PCT No.: PCT/US2010/061021
§ 371 (c)(1),
(2), (4) Date: May 4, 2012

(87) PCT Pub. No.: WO2011/087717
PCT Pub. Date: Jul. 21, 2011

(65) Prior Publication Data
US 2012/0252997 A1      Oct. 4, 2012

Related U.S. Application Data

(60) Provisional application No. 61/289,046, filed on Dec. 22, 2009.

(51) Int. Cl.
C07C 69/612      (2006.01)
C07C 311/09     (2006.01)
C07C 69/653      (2006.01)
C07C 323/49      (2006.01)
C07F 7/18           (2006.01)
C07F 9/38           (2006.01)
C07F 9/40           (2006.01)
C08F 220/26      (2006.01)
C08F 220/38      (2006.01)
D06M 15/256    (2006.01)
D21H 21/16      (2006.01)

(52) U.S. Cl.
CPC ............. C07C 311/09 (2013.01); C07C 69/653 (2013.01); C07C 323/49 (2013.01); C07F 7/1836 (2013.01); C07F 9/3882 (2013.01); C07F 9/4056 (2013.01); C08F 220/26 (2013.01); C08F 220/38 (2013.01); D06M 15/256 (2013.01); D06M 2200/11 (2013.01); D06M 2200/12 (2013.01); D21H 21/16 (2013.01)
USPC .......................................... 560/221; 528/271

(58) Field of Classification Search
CPC ...... C07C 33/46; C07C 311/09; C07C 69/54; C08F 220/26
See application file for complete search history.

(56) References Cited

U.S. PATENT DOCUMENTS

| | | | |
|---|---|---|---|
| 3,458,571 A | 7/1969 | Tokoli | |
| 5,688,848 A | 11/1997 | Cella | |
| 6,664,354 B2 | 12/2003 | Savu | |
| 6,852,781 B2 | 2/2005 | Savu | |
| 7,268,197 B2 | 9/2007 | Moore | |
| 7,345,123 B2 | 3/2008 | Qiu | |
| 7,361,782 B2 | 4/2008 | Klun | |
| 7,396,866 B2 | 7/2008 | Jariwala | |
| 2003/0139549 A1 | 7/2003 | Savu | |
| 2005/0143541 A1 | 6/2005 | Caldwell | |
| 2008/0306238 A1 | 12/2008 | Jariwala | |
| 2010/0227148 A1 | 9/2010 | Jariwala | |
| 2012/0071626 A1 | 3/2012 | Yang | |

FOREIGN PATENT DOCUMENTS

EP      2497762      9/2012

OTHER PUBLICATIONS

Zaragoza Dorwald, Side Reactions in Organic Synthesis, 2005, Wiley-VCH Verlag GmbH & Co. KGaA, Weinheim, Preface. p. IX.*
Hartmann, "Acrylic Copolymers with Perfluoroalkylated Biphenyl Side Groups: Correlation Structure-Surface Properties", Macromolecules, Oct. 3, 2006, vol. 39, No. 20, pp. 6975-6982.
Kirmse, "Carbenes and the O—H Bond: Hydroxyalkyl-Substituted Arylcarbenes", Journal of Organic Chemistry, Apr. 1990, vol. 55, No. 8, pp. 2325-2332.
Schwertfeger, "Monoprotection of Diols as a Key Step for the Selective Synthesis of Unequally Disubstituted Diamondoids (Nanodiamonds)", Journal of Organic Chemistry, Oct. 3, 2008, vol. 73, No. 19, pp. 7789-7792.
Yoshino, "Synthesis of novel highly heat-resistant fluorinated silane coupling agents", Journal of Fluorine Chemistry, Aug. 2006, vol. 127, No. 8, pp. 1058-1065.
XP002629836, Abstract for "Benzenemethanamine, 4-[(2,2,2-trifluoroethoxy)methyl]-", Feb. 26, 2007.
XP002629834, Abstract for "[1,1'-Biphenyl]-2-methanamine, 4'-[(2,2,2-trifluoroethoxy)methyl]-", Nov. 15, 2007.
XP002629835, Abstract for "Benzenemethanamine, 2-[(2,2,2-trifluoroethoxy)methyl]-", Nov. 15, 2007.
XP002629833, Abstract for "Benzenemethanamine, 3-[(2,2,2-trifluoroethoxy)methyl]-", Nov. 19, 2007.
International Search Report for PCT/US2010/061021, mailed on May 4, 2011, 4 pages.

* cited by examiner

*Primary Examiner* — Paul A Zucker
(74) *Attorney, Agent, or Firm* — Jean A. Lown

(57) ABSTRACT

Fluorinated arylene-containing compounds and fluorinated polymers formed from fluorinated arylene-containing compounds, and methods are described. Fluorinated polymers formed from fluorinated arylene-containing compound can be used to provide a low energy surface.

15 Claims, No Drawings

FLUORINATED ARYLENE-CONTAINING COMPOUNDS, METHODS, AND POLYMERS PREPARED THEREFROM

CROSS REFERENCE TO RELATED APPLICATIONS

This application is a national stage filing under 35 U.S.C. 371 of PCT/US2010/061021, filed Dec. 17, 2010, which claims priority to U.S. Provisional Application No. 61/289,046, filed Dec. 22, 2009, the disclosure of which is incorporated by reference in its/their entirety herein.

BACKGROUND

Fluorinated polymeric materials have been prepared previously that can be used in applications where enhanced oil and water repellency are desirable. Some of these fluorinated polymeric materials have included perfluorooctyl groups. Certain perfluorooctyl-containing compounds tend to bio-accumulate in living organisms. This tendency has been cited as a potential concern regarding some fluorochemical materials. New fluorochemical materials that can be effectively eliminated from the body and that provide effective water and oil repellency are desired.

SUMMARY

Fluorinated arylene-containing compounds, methods (e.g., methods of making) and fluorinated polymers prepared from certain of these arylene-containing compounds are described. Fluorinated polymers that are prepared from certain of the arylene-containing compounds described herein can be used to provide a low energy surface that is repellent to oil and water, for example.

In one aspect of the invention, an arylene-containing compound of Formula (I) is provided.

  (I)

In Formula (I), the group Ar is a phenylene or diphenylene. The group Rf is a perfluoroalkyl with optional O or N within the chain. The group L is selected from —O—, —SO$_2$—, —CH$_2$—O—, —C$_2$H$_4$—O—, —C$_2$H$_4$—S—, and —SO$_2$—N(R$^1$)—. The group R$^1$ is a C1-C4 alkyl.

In Formula (I), the groups Y and Q are selected as follows. When Y is selected from —O—, —S—, or —NH—, then Q is selected from: —H, —C$_n$H$_{2n}$—OH, —C(O)—C$_b$H$_{2b+1}$, —C(O)—C$_n$H$_{2n}$—OH, —C(O)—O—C$_n$H$_{2n}$—OH, —C(O)—C(R$^2$)=CH$_2$, —C$_n$H$_{2n}$—O—C(O)—C(R$^2$)=CH$_2$, —C(O)—C$_n$H$_{2n}$—O—C(O)—C(R$^2$)=CH$_2$, —C(O)—NH—C$_n$H$_{2n}$—O—C(O)—C(R$^2$)=CH$_2$, —C$_m$H$_{2m}$—O—C(O)—NH—C$_n$H$_{2n}$—O—C(O)—C(R$^2$)=CH$_2$, —C(O)—C$_m$H$_{2m}$—O—C(O)—NH—C$_n$H$_{2n}$—O—C(O)—C(R$^2$)=CH$_2$, and —(CH$_2$)$_3$Si(OR$^4$)$_3$. Or, when Y is —C(O)O—, —CH$_2$—C(O)O—, or —CH$_2$—C(O)NH—, then Q is selected from: —H, —C$_n$H$_{2n}$—OH, —C$_n$H$_{2n}$—O—C(O)—C(R$^2$)=CH$_2$, and —C$_m$H$_{2m}$—O—C(O)—NH—C$_n$H$_{2n}$—O—C(O)—C(R$^2$)=CH$_2$. Or, Y-Q is selected from: —P(O)(OR$^3$)$_2$, and —N$_3$.

In Formula (I), the group R$^2$ is —H or —CH$_3$. The group R$^3$ is —H, —CH$_3$, or —C$_2$H$_5$. The group R$^4$ is a C1-C4 alkyl or —C(O)—CH$_3$. The variable b is an integer of 1 to 20. The variable m is an integer of 2 to 18. The variable n is an integer of 2 to 18.

In one aspect of the invention, the compounds of Formula (I) are (meth)acrylate functionalized arylene-containing compounds wherein: Ar is a phenylene or diphenylene; Rf is a perfluoroalkyl with optional O or N within the chain; L is selected from —O—, —SO$_2$—, —CH$_2$—O—, —C$_2$H$_4$—O—, —C$_2$H$_4$—S—, and —SO$_2$—N(R$^1$)—; R$^1$ is a C1-C4 alkyl. For such (meth)acrylate functionalized arylene-containing compounds, Y and Q are selected as follows. When Y is selected from —O—, —S—, or —NH—, then Q is selected from: —C$_n$H$_{2n}$—O—C(O)—C(R$^2$)=CH$_2$, —C(O)—C$_n$H$_{2n}$—O—C(O)—C(R$^2$)=CH$_2$, —C(O)—NH—C$_n$H$_{2n}$—O—C(O)—C(R$^2$)=CH$_2$, —C$_m$H$_{2m}$—O—C(O)—NH—C$_n$H$_{2n}$—O—C(O)—C(R$^2$)=CH$_2$, and —C(O)—C$_m$H$_{2m}$—O—C(O)—NH—C$_n$H$_{2n}$—O—C(O)—C(R$^2$)=CH$_2$. Or, when Y is —C(O)O—, —CH$_2$—C(O)O—, or —CH$_2$—C(O)NH—, then Q is selected from: —C$_n$H$_{2n}$—O—C(O)—C(R$^2$)=CH$_2$, and —C$_m$H$_{2m}$—O—C(O)—NH—C$_n$H$_{2n}$—O—C(O)—C(R$^2$)=CH$_2$. For such (meth)acrylate functionalized arylene-containing compounds of Formula (I), R$^2$ is —H or —CH$_3$, m is an integer of 2 to 18, and n is an integer of 2 to 18.

In another aspect, a fluorinated polymer is provided that is a reaction product of a plurality of monomers that include a (meth)acrylate functionalized arylene-containing compound of Formula (I) as described above.

In another aspect of the invention, there is provided a method that includes: providing a monosubstituted-arylene compound of Formula (II):

  (II)

wherein: Ar is a phenylene or diphenylene; Rf is a perfluoroalkyl with optional O or N within the chain; L is selected from —O—, —SO$_2$—, —CH$_2$—O—, —C$_2$H$_4$—O—, —C$_2$H$_4$—S—, and —SO$_2$—N(R$^1$)—; R$^1$ is a C1-C4 alkyl; and W is a leaving group; combining the monosubstituted arylene compound of Formula (II) with a nucleophile to form an arylene-containing compound of Formula (I) as shown above, wherein: Ar is a phenylene or diphenylene; Rf is a perfluoroalkyl with optional O or N within the chain; L is selected from —O—, —SO$_2$—, —CH$_2$—O—, —C$_2$H$_4$—O—, —C$_2$H$_4$—S—, and —SO$_2$—N(R$^1$)—; R$^1$ is a C1-C4 alkyl; Y and Q are selected such that: when Y is selected from —O—, —S—, or —NH—, then Q is selected from: —H, —C$_n$H$_{2n}$—OH, —C(O)—C$_b$H$_{2b+1}$, —C(O)—C$_n$H$_{2n}$—OH, —C(O)—C(R$^2$)=CH$_2$, —C(O)—C$_n$H$_{2n}$—O—C(O)—C(R$^2$)=CH$_2$, —C(O)—C$_m$H$_{2m}$—O—C(O)—NH—C$_n$H$_{2n}$—O—C(O)—C(R$^2$)=CH$_2$, and —(CH$_2$)$_3$Si(OR$^4$)$_3$; or Y-Q is selected from: —P(O)(OR$^3$)$_2$, and —N$_3$; R$^2$ is —H or —CH$_3$; R$^3$ is —H, —CH$_3$, or —C$_2$H$_5$; R$^4$ is a C1-C4 alkyl or —C(O)—CH$_3$; b is an integer of 1 to 20; m is an integer of 2 to 18; and n is an integer of 2 to 18. It is noted that this is a subset of the full scope of compounds of Formula (I) presented above. This subset of compounds can be formed directly from a compound of Formula (II), whereas other compounds of Formula (I) can be prepared from these compounds of Formula (I).

DEFINITIONS

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably.

As used herein, the term "or" is generally employed in its usual sense including "and/or" unless the content clearly dictates otherwise. The term "and/or" means one or all of the listed elements or a combination of any two or more of the listed elements.

As used herein, all numbers are assumed to be modified by the term "about" and preferably by the term "exactly." Notwithstanding that the numerical ranges and parameters setting forth the broad scope of the invention are approximations, the numerical values set forth in the specific examples are reported as precisely as possible. All numerical values, however, inherently contain certain errors necessarily resulting from the standard deviation found in their respective testing measurements.

Also herein, the recitations of numerical ranges by endpoints include all numbers subsumed within that range (e.g., 1 to 5 includes 1, 1.5, 2, 2.75, 3, 3.80, 4, 5, etc.).

The term "in the range" includes the endpoints of the stated range.

When a group is present more than once in a formula described herein, each group is "independently" selected, whether specifically stated or not. For example, when more than one $OR^4$ group is present in a formula, each $OR^4$ group is independently selected. Furthermore, if subgroups are contained within groups, such subgroups are also independently selected.

Groupings of alternative elements or embodiments disclosed herein are not to be construed as limitations. Each group member may be referred to and claimed individually or in any combination with other members of the group or other elements found therein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The term "leaving group" refers to an atom or group of atoms that departs with a pair of electrons in heterolytic bond cleavage. Typically, this is a stable anion of a strong acid, such as, for example, halides and sulfonate esters (e.g., chloride, bromide, methanesulfonate).

The term "monosubstituted-arylene compound" refers to a compound in which one of the two leaving groups of an arylene-containing precursor has been replaced by one fluorochemical group.

The term "(meth)acrylate" refers to an acrylate and a methacrylate.

The term "alkyl" refers to a monovalent group that is a radical of an alkane and includes groups that are linear, branched, cyclic, or combinations thereof. The alkyl group typically has 1 to 60 carbon atoms, 1 to 30 carbon atoms, 1 to 20 carbon atoms, 1 to 10 carbon atoms, 1 to 8 carbon atoms, 1 to 6 carbon atoms (for certain embodiments, 3 to 6 carbon atoms), or 1 to 4 carbon atoms. Examples of alkyl groups include, but are not limited to, methyl ("Me"), ethyl ("Et"), n-propyl, isopropyl, n-butyl, isobutyl, tert-butyl, n-pentyl, n-hexyl, cyclohexyl, n-heptyl, n-octyl, and ethylhexyl.

The terms "arylene" or "Ar" refer to a divalent, aromatic, carbocyclic group, specifically, phenylene ($-C_6H_4-$) and diphenylene ($-C_6H_4-C_6H_4-$).

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, naphthyl, acenaphthyl, anthraquinonyl, phenanthryl, anthracenyl, pyrenyl, perylenyl, and fluorenyl.

The term "(CO)" or "(OC)" or "O(C)" or "C(O)" are used interchangeably to refer to a carbonyl group. Similar groups with S instead of O are referred to as sulfonyl groups.

The term "halide" refers to fluoride, chloride, bromide, or iodide.

The term "perfluoroalkyl" refers to an alkyl in which all of the hydrogen atoms are replaced with a fluorine atom.

The term "oxy" refers to the divalent group $-O-$.

The term "sulfonyl" refers to the divalent group $-SO_2-$.

The term "thio" refers to the divalent group $-S-$.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides fluorinated arylene-containing compounds and fluorinated polymers formed from certain fluorinated arylene-containing compounds. Such compounds typically are more repellent (e.g., with respect to water and oil) and provide more durable coatings relative to non-arylene-containing compounds.

In one aspect of the invention, an arylene-containing compound of Formula (I) is provided.

$$Rf-L-CH_2-Ar-CH_2-Y-Q \qquad (I)$$

In Formula (I), the group Ar is a phenylene or diphenylene. The group Rf is a perfluoroalkyl with optional O or N within the chain. The group L is selected from $-O-$, $-SO_2-$, $-CH_2-O-$, $-C_2H_4-O-$, $-C_2H_4-S-$, and $-SO_2-N(R^1)-$. The group $R^1$ is a C1-C4 alkyl.

In Formula (I), the groups Y and Q are selected as follows. When Y is selected from $-O-$, $-S-$, or $-NH-$, then Q is selected from: $-H$, $-C_nH_{2n}-OH$, $-C(O)-C_bH_{2b+1}$, $-C(O)-C_nH_{2n}-OH$, $-C(O)-O-C_nH_{2n}-OH$, $-C(O)-C(R^2)=CH_2$, $-C_nH_{2n}-O-C(O)-C(R^2)=CH_2$, $-C(O)-C_nH_{2n}-O-C(O)-C(R^2)=CH_2$, $-C(O)-NH-C_nH_{2n}-O-C(O)-C(R^2)=CH_2$, $-C_mH_{2m}-O-C(O)-NH-C_nH_{2n}-O-C(O)-C(R^2)=CH_2$, $-C(O)-C_mH_{2m}-O-C(O)-NH-C_nH_{2n}-O-C(O)-C(R^2)=CH_2$, and $-(CH_2)_3Si(OR^4)_3$. Or, when Y is $-C(O)O-$, $-CH_2-C(O)O-$, or $-CH_2-C(O)NH-$, then Q is selected from: $-H$, $-C_nH_{2n}-OH$, $-C_nH_{2n}-O-C(O)-C(R^2)=CH_2$, and $-C_mH_{2m}-O-C(O)-NH-C_nH_{2n}-O-C(O)-C(R^2)=CH_2$. Or, Y-Q is selected from: $-P(O)(OR^3)_2$, and $-N_3$.

In Formula (I), the group $R^2$ is $-H$ or $-CH_3$. The group $R^3$ is $-H$, $-CH_3$, or $-C_2H_5$. The group $R^4$ is a C1-C4 alkyl or $-C(O)-CH_3$. The variable b is an integer of 1 to 20. The variable m is an integer of 2 to 18. The variable n is an integer of 2 to 18.

The group Ar is a phenylene or diphenylene. In certain embodiments, the group Ar is diphenylene.

The group Rf is a perfluoroalkyl with optional O or N within the chain. Suitable perfluoroalkyl groups often have 1 to 60 carbon atoms, 1 to 30 carbon atoms, 1 to 20 carbon atoms, 1 to 10 carbon atoms, 1 to 8 carbon atoms, 1 to 6 carbon atoms (for certain embodiments 3 to 6 carbon atoms), or 1 to 4 carbon atoms. In certain embodiments, the Rf group is of the formula $C_xF_{2x+1}(OC_yF_{2y})_aOC_pF_{2p}$—, wherein x is 1 to 4, y is 1 to 4, p is 1 to 4, and a is 0 to 20 (for certain embodiments, 4 to 20), wherein in any one molecule each variable is independently selected. In certain embodiments, the Rf group is of the formula $C_3F_7(OCF_2CF(CF_3))_aOCF(CF_3)$—, wherein a is 4 to 20.

In many embodiments, the group Rf is —$C_3F_7$, —$C_4F_9$, —$C_6F_{13}$, or —$C_8F_{17}$. More particularly, the Rf is —$C_3F_7$, —$C_4F_9$, or —$C_6F_{13}$. Even more particularly, the Rf is —$C_4F_9$ or —$C_6F_{13}$.

The group L is selected from —O— (an oxy group), —$SO_2$— (a sulfonyl group), —$CH_2$—O—, —$C_2H_4$—O—, —$C_2H_4$—S—, and —$SO_2$—$N(R^1)$—. In certain embodiments, the group L is selected from —$CH_2$—O—, —$C_2H_4$—O—, and —$SO_2$—$N(R^1)$—. In certain embodiments, L is —$SO_2$—$N(R^1)$— or —$C_2H_4$—O—.

The groups Y and Q are selected such that, in certain embodiments, when Y is selected from —O—, —S— (a thio group), or —NH—, then Q is selected from: —H (thereby resulting in an —OH, —SH, or —$NH_2$ group for Y-Q), —$C_nH_{2n}$—OH, —C(O)—$C_bH_{2b+1}$, —C(O)—$C_nH_{2n}$—OH, —C(O)—O—$C_nH_{2n}$—OH, —C(O)—$C(R^2)$=$CH_2$, —$C_nH_{2n}$—O—C(O)—$C(R^2)$=$CH_2$, —C(O)—$C_nH_{2n}$—O—C(O)—$C(R^2)$=$CH_2$, —C(O)—NH—$C_nH_{2n}$—O—C(O)—$C(R^2)$=$CH_2$, —$C_mH_{2m}$—O—C(O)—NH—$C_nH_{2n}$—O—C(O)—$C(R^2)$=$CH_2$, —C(O)—$C_mH_{2m}$—O—C(O)—NH—$C_nH_{2n}$—O—C(O)—$C(R^2)$=$CH_2$, and —$(CH_2)_3Si(OR^4)_3$.

In certain embodiments, the groups Y and Q are selected such that when Y is selected from —O—, —S—, or —NH—, then Q is selected from: —H, —$C_nH_{2n}$—OH, —C(O)—$C_bH_{2b+1}$, —C(O)—$C_nH_{2n}$—OH, —C(O)—$C(R^2)$=$CH_2$, —C(O)—$C_nH_{2n}$—O—C(O)—$C(R^2)$=$CH_2$, —C(O)—$C_mH_{2m}$—O—C(O)—NH—$C_nH_{2n}$—O—C(O)—$C(R^2)$=$CH_2$, and —$(CH_2)_3Si(OR^4)_3$.

In certain other embodiments, the groups Y and Q are selected such that when Y is selected from —O—, —S—, or —NH—, then Q is selected from: —$C_nH_{2n}$—O—C(O)—$C(R^2)$=$CH_2$, —C(O)—$C_nH_{2n}$—O—C(O)—$C(R^2)$=$CH_2$, —C(O)—NH—$C_nH_{2n}$—O—C(O)—$C(R^2)$=$CH_2$, —$C_mH_{2m}$—O—C(O)—NH—$C_nH_{2n}$—O—C(O)—$C(R^2)$=$CH_2$, and —C(O)—$C_mH_{2m}$—O—C(O)—NH—$C_nH_{2n}$—O—C(O)—$C(R^2)$=$CH_2$.

In certain embodiments, the groups Y and Q are selected such that when Y is selected from —O— or —S—, then Q is selected from: —H, —$C_nH_{2n}$—OH, —C(O)—$C_nH_{2n}$—OH, —C(O)—O—$C_nH_{2n}$—OH, —C(O)—$C(R^2)$=$CH_2$, —$C_nH_{2n}$—O—C(O)—$C(R^2)$=$CH_2$, —C(O)—$C_nH_{2n}$—O—C(O)—$C(R^2)$=$CH_2$, —C(O)—NH—$C_nH_{2n}$—O—C(O)—$C(R^2)$=$CH_2$, —$C_mH_{2m}$—O—C(O)—NH—$C_nH_{2n}$—O—C(O)—$C(R^2)$=$CH_2$, —C(O)—$C_mH_{2m}$—O—C(O)—NH—$C_nH_{2n}$—O—C(O)—$C(R^2)$=$CH_2$, and —$(CH_2)_3Si(OR^4)_3$.

In certain other embodiments, the groups Y and Q are selected such that when Y is selected from —O— or —S—, then Q is selected from: —H, —C(O)—$C(R^2)$=$CH_2$, —$C_nH_{2n}$—OH, —$C_nH_{2n}$—O—C(O)—$C(R^2)$=$CH_2$, —C(O)—$C_nH_{2n}$—OH, —C(O)—$C_nH_{2n}$—O—C(O)—$C(R^2)$=$CH_2$, and —C(O)—$C_mH_{2m}$—O—C(O)—NH—$C_nH_{2n}$—O—C(O)—$C(R^2)$=$CH_2$.

Or, the groups Y and Q are selected such that, in certain embodiments, when Y is —C(O)O—, —$CH_2$—C(O)O—, or —$CH_2$—C(O)NH—, then Q is selected from: —H, —$C_nH_{2n}$—OH, —$C_nH_{2n}$—O—C(O)—$C(R^2)$=$CH_2$, and —$C_mH_{2m}$—O—C(O)—NH—$C_nH_{2n}$—O—C(O)—$C(R^2)$=$CH_2$.

Or, in other embodiments, the groups Y and Q are selected such that when Y is —C(O)O—, —$CH_2$—C(O)O—, or —$CH_2$—C(O)NH—, then Q is selected from: —$C_nH_{2n}$—O—C(O)—$C(R^2)$=$CH_2$, and —$C_mH_{2m}$—O—C(O)—NH—$C_nH_{2n}$—O—C(O)—$C(R^2)$=$CH_2$.

Or, in certain embodiments, Y-Q is selected from —P(O)$(OR^3)_2$, —$N_3$, and —$NH_2$. In certain embodiments, Y-Q is selected from —P(O)$(OR^3)_2$ and —$N_3$. In certain embodiments, Y-Q is —P(O)$(OR^3)_2$.

The group $R^1$ is a C1-C4 alkyl. In certain embodiments, $R^1$ is —$CH_3$.

The group $R^2$ is —H or —$CH_3$.

The group $R^3$ is —H, —$CH_3$, or —$C_2H_5$.

The group $R^4$ is a C1-C4 alkyl or —C(O)—$CH_3$. In certain embodiments, the group $R^4$ is a C1-C4 alkyl. In certain embodiments, $R^4$ is —$CH_3$.

The variable b is an integer of 1 to 20.

The variable m is an integer of 2 to 18. In certain situations, m is 2 to 12, or m is 2 to 6.

The variable n is an integer of 2 to 18. In certain situations, n is 2 to 12, or n is 2 to 6.

In certain embodiments of Formula (I), compounds include groups wherein: Ar is a diphenylene; Rf is —$C_4F_9$ or —$C_6F_{13}$; L is —$SO_2$—$N(R^1)$— or —$C_2H_4$—O—; Y and Q are selected such that when Y is selected from —O— or —S—, then Q is selected from: —H, —C(O)—$C(R^2)$=$CH_2$, —$C_nH_{2n}$—OH, —$C_nH_{2n}$—O—C(O)—$C(R^2)$=$CH_2$, —C(O)—$C_nH_{2n}$—OH, —C(O)—$C_nH_{2n}$—O—C(O)—$C(R^2)$=$CH_2$, and —C(O)—$C_mH_{2m}$—O—C(O)—NH—$C_nH_{2n}$—O—C(O)—$C(R^2)$=$CH_2$; $R^1$ is —$CH_3$; $R^2$ is —H or —$CH_3$; m is an integer of 2 to 6; and n is an integer of 2 to 6.

In certain embodiments of Formula (I), the compounds are (meth)acrylate functionalized arylene-containing compounds wherein: Ar is a phenylene or diphenylene; Rf is a perfluoroalkyl with optional O or N within the chain; L is selected from —O—, —$SO_2$—, —$CH_2$—O—, —$C_2H_4$—O—, —$C_2H_4$—S—, and —$SO_2$—$N(R^1)$—; $R^1$ is a C1-C4 alkyl; Y and Q are selected such that when Y is selected from —O—, —S—, or —NH—, then Q is selected from: —$C_nH_{2n}$—O—C(O)—$C(R^2)$=$CH_2$, —C(O)—$C_nH_{2n}$—O—C(O)—$C(R^2)$=$CH_2$, —C(O)—NH—$C_nH_{2n}$—O—C(O)—$C(R^2)$=$CH_2$, —$C_mH_{2m}$—O—C(O)—NH—$C_nH_{2n}$—O—C(O)—$C(R^2)$=$CH_2$, and —C(O)—$C_mH_{2m}$—O—C(O)—NH—$C_nH_{2n}$—O—C(O)—$C(R^2)$=$CH_2$; or when Y is —C(O)O—, —$CH_2$—C(O)O—, or —$CH_2$—C(O)NH—, then Q is selected from: —$C_nH_{2n}$—O—C(O)—$C(R^2)$=$CH_2$, and —$C_mH_{2m}$—O—C(O)—NH—$C_nH_{2n}$—O—C(O)—$C(R^2)$=$CH_2$; $R^2$ is —H or —$CH_3$; m is an integer of 2 to 18; and n is an integer of 2 to 18.

Some exemplary and preferred compounds of Formula (I) are of the structures:

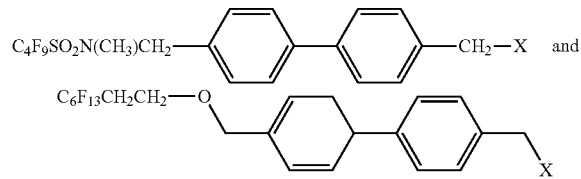

wherein X is selected from: —$SC_2H_4$—O—C(O)—CH=$CH_2$, —O—C(O)—CH=$CH_2$, —O—C(O)—$CH_2$O—C(O)—CH=$CH_2$, —$SC_2H_4$—O—C(O)—C (CH₃)=CH₂, —O—C(O)—(CH₂)₅O—C(O)—C(CH₃)=CH₂, —O—C(O)—CH₂O—C(O)—C(CH₃)=CH₂, and —OC(O)—CH₂O—C(O)—NH—C₂H₄O—C(O)—CH=CH₂.

Particularly preferred compounds are as follows:

are as discussed herein for compounds of Formula (I). Exemplary and preferred L groups of compounds of Formula (II) are as discussed herein for compounds of Formula (I). Exemplary and preferred R¹ groups of compounds of Formula (II) are as discussed herein for compounds of Formula (I).

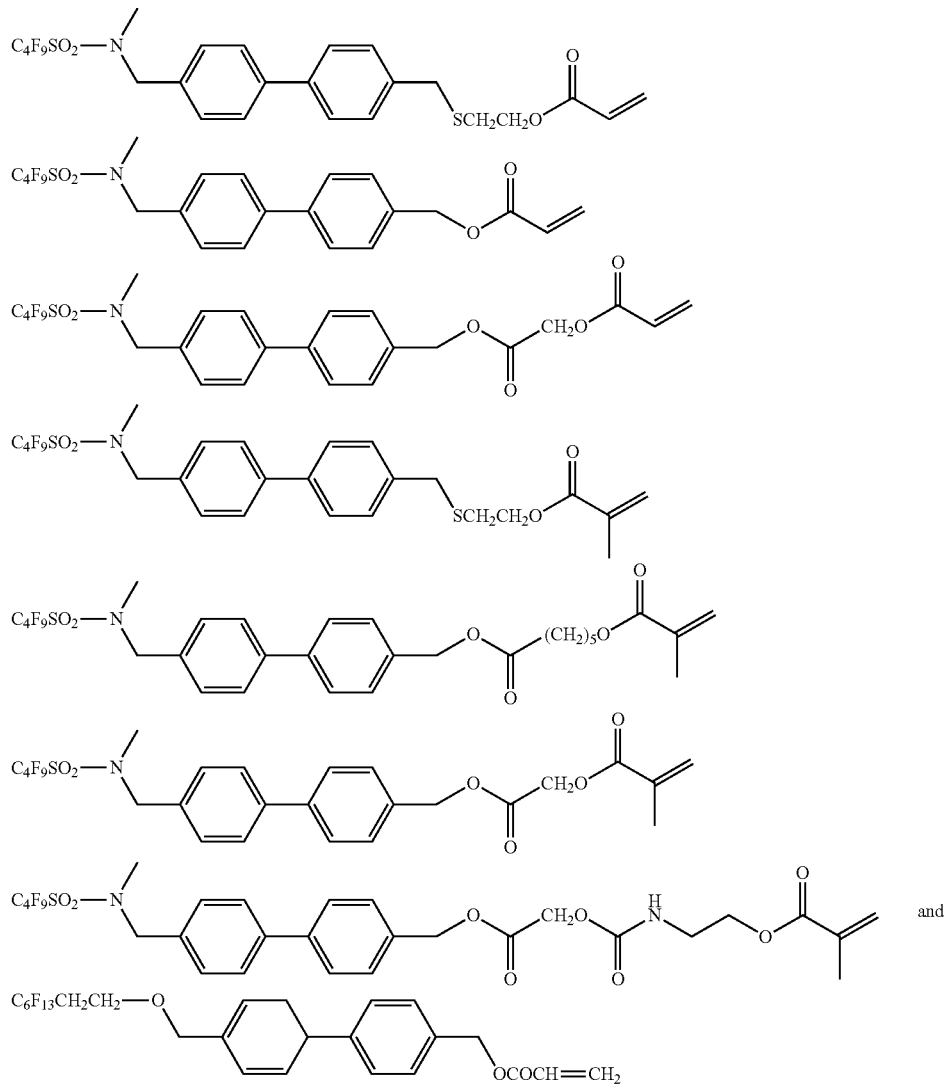

The compounds of Formula (I) can be prepared by various suitable processes. In one embodiment, compounds of Formula (I) can be made using a monosubstituted-arylene compound of Formula (II):

Rf-L-CH₂—Ar—CH₂—W    (II)

wherein: Ar is a phenylene or diphenylene (in certain embodiments, Ar is diphenylene); Rf is a perfluoroalkyl with optional O or N within the chain; L is selected from —O—, —SO₂—, —CH₂—O—, —C₂H₄—O—, —C₂H₄—S—, and —SO₂—N(R¹)—; R¹ is a C1-C4 alkyl; and W is a leaving group.

In certain embodiments of Formula (II), the group W is preferably selected from halide and pseudohalide groups. More preferably, the group W is selected from Cl, Br, or —OSO₂R⁵, wherein R⁵ is an alkyl, aryl, fluorinated alkyl, or combination thereof (e.g., methyl, tolyl, and benzyl). Exemplary and preferred Rf groups of compounds of Formula (II)

In certain embodiments, certain compounds of Formula (I) can be prepared directly from a compound of Formula (II) by replacing leaving group W. For example, a monosubstituted-arylene compound of Formula (II) can be combined with a nucleophile to form an arylene-containing compound of Formula (I), as described in greater detail below.

In other embodiments, certain compounds of Formula (I) can be used as intermediates to prepare other compounds of Formula (I). For example, certain compounds of Formula (I) can be made from other compounds of Formula (I) that include an active hydrogen on O, S, or N (e.g., OH, SH, NH₂). In one embodiment, an —OC(O)CH₃ group can be converted to an —OH group, which can be converted to an acrylate group, which are all —Y-Q groups in compounds of Formula (I).

The monosubstituted-arylene compound of Formula (II) as described above can be prepared using a method that involves combining a base with a compound of Formula (III) Rf-L-H, a compound of Formula (IV) W—CH$_2$—Ar—CH$_2$—W, and an organic solvent. Preferably, the compounds of Formulas (III) and (IV) are in a solution with the organic solvent and the base is added to the solution. The reaction (e.g., addition of base to solution of compounds of Formulas (III) and (IV)) is carried out over a period of time effective to form the monosubstituted-arylene compound of Formula (II).

In compounds of starting material Formula (III): Rf is a perfluoroalkyl with optional O or N within the chain (with exemplary and preferred Rf groups as discussed herein for compounds of Formula (I)); and L is selected from —O—, —SO$_2$—, —CH$_2$—O—, —C$_2$H$_4$—O—, —C$_2$H$_4$—S—, and —SO$_2$—N(R$^1$)— wherein R$^1$ is a C1-C4 alkyl (preferably, R$^1$ is —CH$_3$). In certain embodiments, the group L is selected from —CH$_2$—O—, —C$_2$H$_4$—O—, and —SO$_2$—N(R$^1$)—. In certain embodiments, L is —SO$_2$—N(R$^1$)— or —C$_2$H$_4$—O—.

In compounds of starting material Formula (IV): Ar is a phenylene or diphenylene (preferably, a diphenylene); and W is a leaving group (with exemplary and preferred W groups as discussed herein for compounds of Formula (II)). In compounds of Formula (II), the W groups can be independently selected.

In certain embodiments of the method of making a monosubstituted-arylene compound of Formula (II) (e.g., for sulfonamide compounds), the base is more basic than sodium carbonate. In certain embodiments of this method, the base is an organic base. In certain embodiments of this method, the organic base is selected from 1,8-diazabicyclo[5.4.0]undec-7-ene, 1,5-diazabicyclo[4.3.0]non-5-ene, and (R$^4$)$_4$NOH wherein R$^4$ is C1-C4 alkyl. In certain methods, the base is an inorganic base, such as NaOH or NaH.

In certain embodiments of the method of making a monosubstituted-arylene compound of Formula (II), the organic solvent is selected from acetone, THF, DMF, toluene, or mixtures thereof. Exemplary organic solvents are ones that will dissolve the monosubstituted-arylene compound of Formula (II) at a temperature of, e.g., 25° C. to 50° C. The temperature of the reaction between starting materials of Formulas (III) and (IV) is not particularly critical. That is, a range of temperatures can be used as can be determined by one of skill in the art that would be practical, effective, and efficient. For example, temperatures down to 0° C. can be used, as well as refluxing temperatures of the solvent(s). Typically, a temperature of 25° C. to 50° C. is used.

In certain embodiments of the method of making a monosubstituted-arylene compound of Formula (II), the base is added to a solution of the starting materials of Formulas (III) and (IV). Alternatively, however, the base can be added to one of the reactants, typically the starting material of Formula (III), and then the mixture can be added to starting material of Formula (IV) W—CH$_2$—Ar—CH$_2$—W. Typically, the base (whether added to a solution of both starting materials or added in combination with the starting material of Formula (III)) is added relatively slowly such that the compound of Formula (IV) W—CH$_2$—Ar—CH$_2$—W is in excess relative to the reactive nucleophile. Typically, the base is added over a period of at least 1 hour, and often at least 2 hours, although shorter periods of time can be used.

In certain embodiments of the method of making a monosubstituted-arylene compound of Formula (II), such compound is formed in a yield of at least 70 mole-%.

In certain embodiments of the method of making a monosubstituted-arylene compound of Formula (II), such compound is formed at a purity level of at least 70 wt-%, based on the total weight of solids.

In certain embodiments of the method of making a monosubstituted-arylene compound of Formula (II), such compound is isolated from the reaction mixture prior to further use (e.g., prior to contacting it with the nucleophile in the method of making a compound of Formula (I)).

The compounds of Formula (I) that can be formed directly reacting a nucleophile with the group W of a compound of Formula (II) including those wherein: Ar is a phenylene or diphenylene; Rf is a perfluoroalkyl with optional O or N within the chain; L is selected from —O—, —SO$_2$—, —CH$_2$—O—, —C$_2$H$_4$—O—, —C$_2$H$_4$—S—, and —SO$_2$—N(R$^1$)—; R$^1$ is a C1-C4 alkyl; Y and Q are selected such that: when Y is selected from —O—, —S—, or —NH—, then Q is selected from: —H, —C$_n$H$_{2n}$—OH, —C(O)—C$_b$H$_{2b+1}$, —C(O)—C$_n$H$_{2n}$—OH, —C(O)—C(R$^2$)=CH$_2$, —C(O)—C$_n$H$_{2n}$—O—C(O)—C(R$^2$)=CH$_2$, —C(O)—C$_m$H$_{2m}$—O—C(O)—NH—C$_n$H$_{2n}$—O—C(O)—C(R$^2$)=CH$_2$, and —(CH$_2$)$_3$Si(OR$^4$)$_3$; or Y-Q is selected from: —P(O)(OR$^3$)$_2$, and —N$_3$; R$^2$ is —H or —CH$_3$; R$^3$ is —H, —CH$_3$, or —C$_2$H$_5$; R$^4$ is a C1-C4 alkyl or —C(O)—CH$_3$; b is an integer of 1 to 20; m is an integer of 2 to 18; and n is an integer of 2 to 18.

In embodiments of Formula (I) wherein Y-Q is —OH or —SH, although they can be made directly from compounds of Formula (II) by displacing W, the yields and purity would be low unless a large excess of the —OH or —SH were present. If not, the initial adduct could displace another W. Thus, preferably, O and S are masked using acetate and thiourea to make indirectly compounds of Formula (I) wherein Y-Q is —OH or —SH.

In certain embodiments of this direct method of forming a compound of Formula (I) from a compound of Formula (II), the nucleophile is, or is derived from (e.g., by ionization of), a compound selected from one or more of the following: HO—C$_n$H$_{2n}$—OH, wherein n is an integer of 2 to 18; $^-$S—C$_n$H$_{2n}$—OH anion, wherein n is an integer of 2 to 18; HO—C$_n$H$_{2n}$—O—C(O)—C(R$^2$)=CH$_2$, wherein R$^2$ is —H or —CH$_3$; $^-$S—(CH$_2$)$_3$Si(OMe)$_3$ anion; $^-$S—(CH$_2$)$_3$Si(OEt)$_3$ anion; P(OR$^3$)$_3$, wherein R$^3$ is —H, —CH$_3$, or —C$_2$H$_5$; $^-$O—C(O)—C$_{n-1}$H$_{2n-2}$—OH anion, wherein n is an integer of 2 to 18 (which can be derived, for example, from a salt, acid, or lactone); $^-$O—C(O)—C$_b$H$_{2b+1}$ anion, wherein b is an integer of 1 to 20; $^-$S—C(O)—C$_b$H$_{2b+1}$ anion, wherein b is an integer of 1 to 20; NH$_2$C(S)NH$_2$; $^-$N$_3$ anion; and $^-$CH—(C(O)OR$^1$)$_2$ anion, wherein R$^1$ is a C1-C4 alkyl.

In this reaction between a monosubstituted-arylene compound of Formula (II) and a nucleophile, the nucleophile is typically used in a molar equivalent amount or molar excess amount relative to the monosubstituted-arylene compound. Such reaction can be carried out in a solvent (which can include water), typically an organic solvent (such as acetone, DMF, MEK, THF, toluene, methanol, including mixtures such as a toluene-THF mixture), at an effective temperature (ranging, for example, from room temperature to 150° C., and often at 50° C.), for an effective amount of time (ranging, for example, from 1 hour to 24 hours, and often 2 to 4 hours). Various conditions suitable for carrying out nucleophilic substitution reactions can be used, as known to one of skill in the art, and as exemplified in the Examples Section.

The compounds of Formula (I) are advantageous at least because the arylene group gives a more repellent and durable coating relative to non-arylene-containing compounds. It is believed that this is because of higher organization and melting points.

The compounds of Formula (I) can be used as additives (e.g., as melt additives) or as precursors to polymers. In one aspect, a fluorinated polymer is provided that is a reaction product of a plurality of monomers that include a (meth)

acrylate functionalized arylene-containing compound of Formula (I) as described above. The polymerization reaction can be carried out using standard conditions well known to those of skill in the art.

The fluorinated polymers can be dissolved in a suitable solvent to prepare a coating composition that can be applied to a surface of a substrate. The solvent can be removed after application of the coating to the substrate. Suitable solvents include, but are not limited to, alcohols, esters, ethers, glycol ethers, amides, ketone, hydrocarbons, chlorohydrocarbons, hydrofluoroethers, chlorocarbons, and mixtures thereof. The coating compositions often contain 0.1 to 10 weight percent, 0.1 to 5 weight percent, or 0.5 to 5 weight percent fluorinated polymer.

The coating composition can be applied to any suitable substrate. In some embodiments, the coating composition is applied to fibers such as woven fabrics, knit fabrics, non-woven fabrics, textiles, carpets, leather, or paper. Other substrates include, but are not limited to, glass, ceramic, masonry, concrete, natural stone, metals, wood, plastic, and painted surfaces. The substrates can have flat or curved surfaces and can be particles or granules.

The coating compositions can be applied to the substrate using any suitable application method such as, for example, spraying, padding, dipping, roll coating, or brushing. When coating flat substrates of appropriate size, knife-coating or bar-coating methods can be used to ensure uniform coatings of the substrate. The thickness of the coating can be any suitable thickness needed to achieve the desired properties such as the desired repellency. This thickness of the coating can often be adjusted without compromising the desirable characteristics of the substrate. For example, the coatings can be in the range of a few microns (e.g., 1 to 5 microns) up to 50 microns or even greater, up to 30 microns, up to 20 microns, or up to 10 microns.

The polymer can also be heated and then extruded or molded. Any methods know in the art can be used. In some embodiments, the fluorinated polymers are extruded to form a clear film that is suitable for use in optical applications. The polymers are often extruded at temperatures in the range of 150° C. to 300° C. or in the range of 150° C. to 250° C.

The fluorinated polymers can have low surface energy as indicated by its water and oil repellency. Compared to many non-fluorinated polymers, the contact angle with both water and hexadecane tends to be greater. That is, these polymers can be used to provide a surface that is water and oil repellant. Such surfaces tend to remain cleaner and are more easily cleaned than many non-fluorinated surfaces. This property is also useful in providing release for pressure sensitive adhesives.

For certain embodiments, fluorinated polymers have a receding water-contact angle of at least 90, and preferably at least 100. For certain embodiments, fluorinated polymers have a receding hexane-contact angle of at least 60, and preferably at least 70.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

All parts, percentages, ratios, etc. in the examples and the rest of the specification are by weight, unless noted otherwise.

Solvents and other reagents used were obtained from Aldrich Chemical Company, Milwaukee, Wis. unless otherwise noted.

Materials

N-Methylperfluorobutanesulfonamide was prepared as described in Example 1 of U.S. Pat. No. 6,664,354 (Savu et al.).

4,4'-Bis(chloromethyl)biphenyl was obtained from Aldrich Chemical Company, Milwaukee, Wis.

$(C_4H_9)_4NOH$ was obtained from Aldrich Chemical Company, Milwaukee, Wis.

Acetone was obtained from VWR Scientific, Batavia, Ill.

Ethyl acetate was obtained from EMD Chemicals USA, Gibbstown N.J.

Anhydrous magnesium sulfate was obtained from Aldrich Chemical Company, Milwaukee, Wis.

$HO(CH_2)_6OH$ was obtained from Aldrich Chemical Company, Milwaukee, Wis.

Cupric acetylacetonate was obtained from Aldrich Chemical Company, Milwaukee, Wis.

Ethylene glycol was obtained from Aldrich Chemical Company, Milwaukee, Wis.

Potassium carbonate was obtained from Aldrich Chemical Company, Milwaukee, Wis.

DMF was obtained from EMD Chemicals USA, Gibbstown, N.J.

$HS(CH_2)_2OH$ was obtained from Aldrich Chemical Company, Milwaukee, Wis.

Sodium acetate was obtained from Aldrich Chemical Company, Milwaukee, Wis.

Monohydrate toluenesulfonic acid was obtained from Aldrich Chemical Company, Milwaukee, Wis.

Ethanol was obtained from EMD Chemicals USA, Gibbstown, N.J.

Epsilon-caprolactone was obtained from Aldrich Chemical Company, Milwaukee, Wis.

$HOCH_2COOH$ was obtained from Aldrich Chemical Company, Milwaukee, Wis.

$C_3F_7CH_2OH$ was obtained from Aldrich Chemical Company, Milwaukee, Wis.

NaH in mineral oil was obtained from Aldrich Chemical Company, Milwaukee, Wis.

Methylene chloride was obtained from EMD Chemicals USA, Gibbstown, N.J.

1H,2H,2H-perfluoro-1-octanol is available from Aldrich Chemical Company, Milwaukee, Wis.

THF was obtained from EMD Chemicals USA, Gibbstown, N.J.

NaOH was obtained from Aldrich Chemical Company, Milwaukee, Wis.

Perfluoromethylmorpholine (PF5052) was obtained from 3M Company, St. Paul, Minn.

Thiourea was obtained from Aldrich Chemical Company, Milwaukee, Wis.

Methyl ethyl ketone was obtained from EMD Chemicals USA, Gibbstown, N.J.

HCl was obtained from Alfa Aesar Ward Hill, Mass.

Acryloyl chloride was obtained from Aldrich Chemical Company, Milwaukee, Wis.

Methacryloyl chloride was obtained from Aldrich Chemical Company, Milwaukee, Wis.

1,2-Dimethoxyethane was obtained from Aldrich Chemical Company, Milwaukee, Wis.

Triethylamine was obtained from EMD Chemicals USA, Gibbstown, N.J.

Isocyanatoethyl methacrylate was obtained from Aldrich Chemical Company, Milwaukee, Wis.

Dibutyltin dilaurate was obtained from Aldrich Chemical Company, Milwaukee, Wis.
VAZO 67 was obtained from Dupont, Wilmington, Del.
Triethyl phosphate was obtained from Aldrich Chemical Company, Milwaukee, Wis.
Trimethylsilyl bromide was obtained from Aldrich Chemical Company, Milwaukee, Wis.
Dichloromethane was obtained from Aldrich Chemical Company, Milwaukee, Wis.
$HS(CH_2)_2Si(OMe)_3$ was obtained from Aldrich Chemical Company, Milwaukee, Wis.
$CH_2(COOEt)_2$ was obtained from Aldrich Chemical Company, Milwaukee, Wis.
Sodium methoxide (25% w/w in methanol) was obtained from Aldrich Chemical Company, Milwaukee, Wis.

Test Methods

Method for Measuring Dynamic Contact Angles

A test solution of polymers prepared according to the invention (typically at about 3% solid in ethyl acetate) was applied to Nylon-6,6 film (available from DuPont, Wilmington, Del.) by dip-coating strips of the film into the test solution. Prior to coating, the film was cleaned with methyl alcohol. Using a small binder clip to hold one end of the nylon film, the strip was immersed in the test solution, and then withdrawn slowly and smoothly from the solution. The coated strip was allowed to air dry in a protected location for a minimum of 30 minutes and then was cured for 10 minutes at 150° C.

Advancing and receding contact angles on the coated nylon film were measured using a CAHN Dynamic Contact Angle Analyzer, Model DCA 322 (a Wilhelmy balance apparatus equipped with a computer for control and data processing commercially available from ATI, Madison, Wis.). Water and hexadecane were used as probe liquids. Values for both water and hexadecane are reported. Larger values of contact angles are indicative of better repellency.

Method for Differential Scanning Calorimeter (DSC) Analysis

A sample (7 to 10 milligrams) of the polymer prepared according to the invention was placed in a TZERO aluminum pan and lid (obtained from TA Instruments, New Castle, Del.) and was analyzed in a TA Q2000 DSC (TA Instruments, New Castle, Del.) under a nitrogen flow of 50 mL per minute. The time-temperature profile of the test was as follows: the sample temperature was first equilibrated at 30° C., and then heated at 20° C. per minute to 290° C., held at 290° C. for 3 minutes, cooled at 20° C. per minute to 30° C., heated at 20° C. per minute to 290° C. Melting temperature, $T_m$, and glass-transition temperature, $T_g$, of polymers were determined.

Example 1

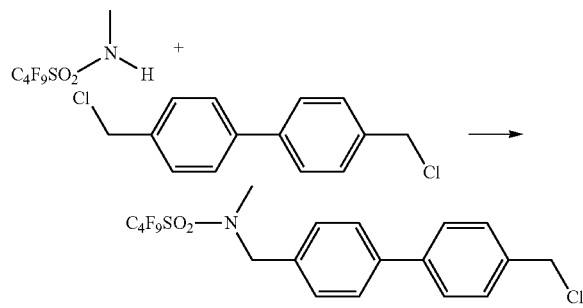

N-methylperfluorobutanesulfonamide, 0.15 mole (mol), 47 grams (g) and 4,4'-bis(chloromethyl)biphenyl (0.15 mol, 37.7 g) were dissolved in 250 mL acetone. The solution was heated to 50° C. $(C_4H_9)_4NOH$ (55% w/w in water, 0.15 mol, 70.8 g) was added slowly during 3 hours (hr) while the solution was kept at 50° C. After the addition was finished, the reaction mixture was kept for another hour at 50° C. The solid was filtered off and washed by 100 milliliters (mL) of acetone. The combined acetone solution was subjected to rotary evaporation to remove the acetone. The solid was re-dissolved into ethyl acetate, washed by water, dried by anhydrous magnesium sulfate. Evaporation of solvent by a rotary evaporator gave 60 g 94% pure product 4-(N-methylperfluorobutanesulfonamidomethyl)-4'-chloromethylbiphenyl.

Example 2

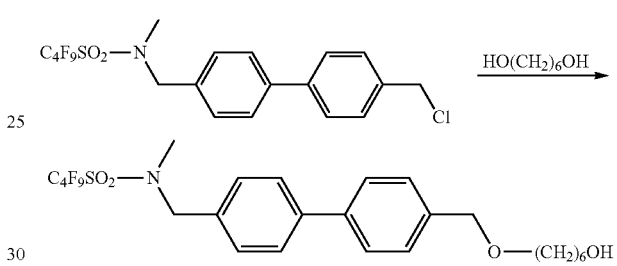

4-(N-methylperfluorobutanesulfonamidomethyl)-4'-chloromethylbiphenyl (0.02 mol, 10.56 g), $HO(CH_2)_6OH$ (0.12 mol, 14.06 g), and cupric acetylacetonate (96%, 0.26 g) were charged into a flask. The solution was heated at 140° C. for 3 hr. The solution was diluted by ethyl acetate, washed by water, dried by anhydrous magnesium sulfate. Evaporation of solvent by a rotary evaporator gave 8.1 g of product 4'-(N-methylperfluorobutanesulfonamidomethyl)-4'-(6-hydroxyhexyloxymethyl) biphenyl.

Example 3

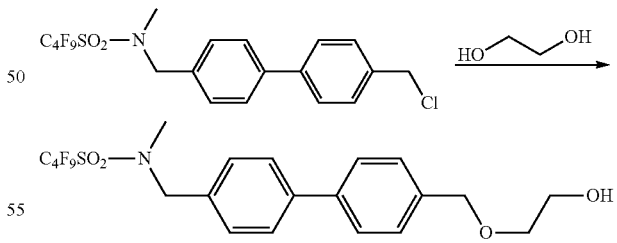

4-(N-methylperfluorobutanesulfonamidomethyl)-4'-chloromethylbiphenyl (0.02 mol, 10.56 g), ethylene glycol (0.2 mol, 13.4 g), and cupric acetylacetonate (96%, 0.26 g) were charged into a flask. The solution was heated at 140° C. for 3 hr. The solution was diluted by ethyl acetate, washed by water, dried by anhydrous magnesium sulfate. Evaporation of solvent by a rotary evaporator gave 10.4 g product 4'-(N-methylperfluorobutanesulfonamidomethyl)-4'-(2-hydroxyethoxymethyl) biphenyl.

Example 4

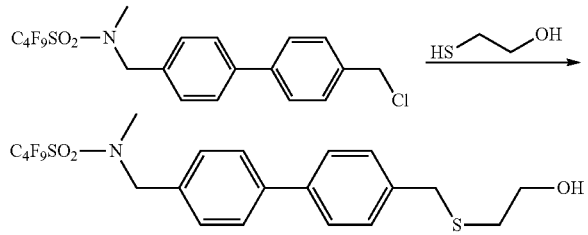

4-(N-methylperfluorobutanesulfonamidomethyl)-4'-chloromethylbiphenyl (0.02 mol, 10.55 g), HS(CH₂)₂OH (0.022 mol, 1.72 g), potassium carbonate (0.03 mol, 4.2 g) and 20 mL DMF were charged into a flask. The solution was stirred at room temperature for 3 hr. The solution was diluted by ethyl acetate, washed by water, dried by anhydrous magnesium sulfate. Evaporation of solvent by a rotary evaporator gave 9.7 g of product 4'-(N-methylperfluorobutanesulfonamidomethyl)-4'-(2-hydroxyethylmercaptomethyl) biphenyl.

Example 5

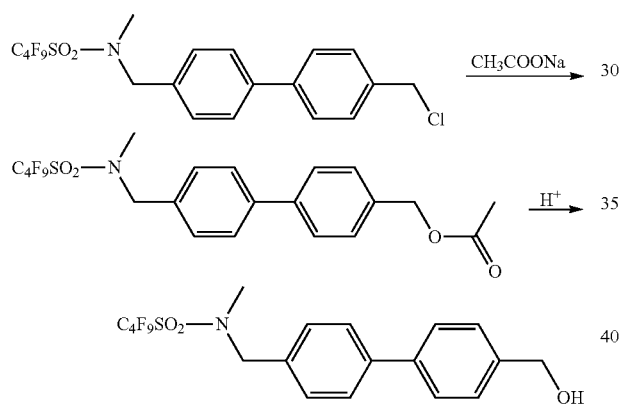

4-(N-methylperfluorobutanesulfonamidomethyl)-4'-chloromethylbiphenyl (0.01 mol, 5.28 g), sodium acetate (0.02 mol, 1.64 g) and 20 mL DMF were charged into a flask. The solution was stirred at 80° C. for 2 hr. The solution was diluted by ethyl acetate, washed by water, dried by anhydrous magnesium sulfate. Evaporation of solvent by a rotary evaporator gave 5.2 g of 4'-(N-methylperfluorobutanesulfonamidomethyl)-4'-(acetoxymethyl) biphenyl. All of the obtained compound, and monohydrate toluenesulfonic acid (0.17 g), 200 mL ethanol were refluxed for 24 hr. The solution was diluted by ethyl acetate, washed by water, dried by anhydrous magnesium sulfate. Evaporation of solvent by a rotary evaporator gave 5.0 g of 4'-(N-methylperfluorobutanesulfonamidomethyl)-4'-hydroxymethyl biphenyl.

Example 6

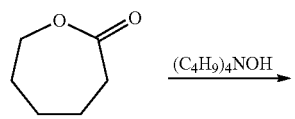

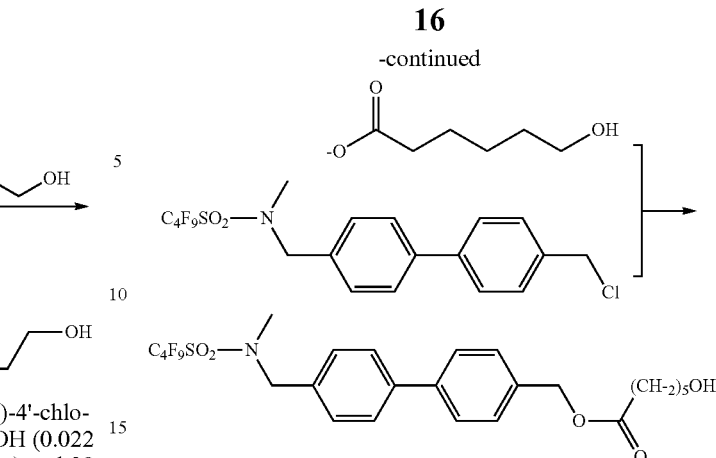

Epsilon-caprolactone (0.012 mol, 1.37 g) and (C₄H₉)₄NOH (55% w/w in water, 0.012 mol, 5.66 g) were mixed and heated at 65° C. for 2 hr. Then, water was evaporated by a rotary evaporator. DMF (20 mL) and 4-(N-methylperfluorobutanesulfonamidomethyl)-4'-chloromethylbiphenyl (0.01 mol, 5.28 g) were added. The solution was stirred at 65° C. for 2 hr. The solution was diluted by ethyl acetate, washed by water, dried by anhydrous magnesium sulfate. Evaporation of solvent by a rotary evaporator gave 5.0 g of 4'-(N-methylperfluorobutanesulfonamidomethyl)-4'-(6-hydroxyhexanoyloxymethyl) biphenyl.

Example 7

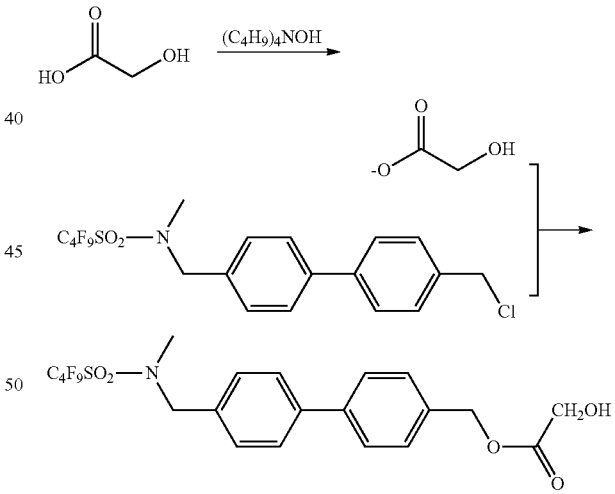

HOCH₂COOH (0.024 mol, 1.38 g) and (C₄H₉)₄NOH (55% w/w in water, 0.024 mol, 11.32 g) were mixed and heated at 65° C. for 2 hr. Then water was evaporated by a rotary evaporator. DMF (20 mL) and 4-(N-methylperfluorobutanesulfonamidomethyl)-4'-chloromethylbiphenyl (0.02 mol, 10.56 g) was added. The solution was stirred at 65° C. for 2 hr. The solution was diluted by ethyl acetate, washed by water, dried by anhydrous magnesium sulfate. Evaporation of solvent by a rotary evaporator gave 10 g of 4'-(N-methylperfluorobutanesulfonamidomethyl)-4'-hydroxyacetyloxymethyl biphenyl.

Example 8

Preparation of 4-(heptafluorobutoxymethyl)-4'-chloromethylbiphenyl

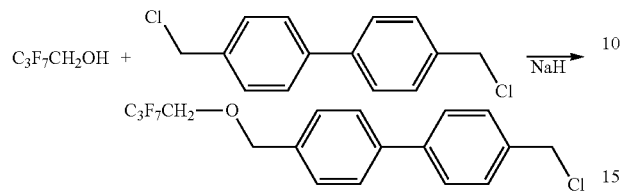

A mixture of 20.0 g (0.1 mol) C$_3$F$_7$CH$_2$OH and 60 mL DMF was treated with 4.0 g of 60% NaH/mineral oil in small portions at <10° C. The resulting solution was added dropwise over 1 hr to a solution of 25.1 g (0.1 mol) 4,4'-bis(chloromethyl)biphenyl in 110 mL DMF at 50° C. After 5 hr, the mixture was poured into 1 liter (L) water and the resulting white solid collected by filtration. GLC (thermal conductivity detector) showed two new materials (5% and 39%) and 50% unreacted starting dichloride. GC/MS confirmed these as 4,4'-bis(heptafluorobutoxymethyl)biphenyl and 4-(heptafluorobutoxymethyl)-4'-chloromethylbiphenyl, respectively. The solid (35.4 g) was dissolved in 600 mL boiling hexane. A granular precipitate (5.8 g) formed on cooling to 23° C. The supernatant liquid was evaporated to yield 17.5 g, 10% diether, 60% monoether and 30% dichloride.

Example 9

Preparation of 4-(heptafluorobutoxymethyl)-4'-hydroxymethylbiphenyl

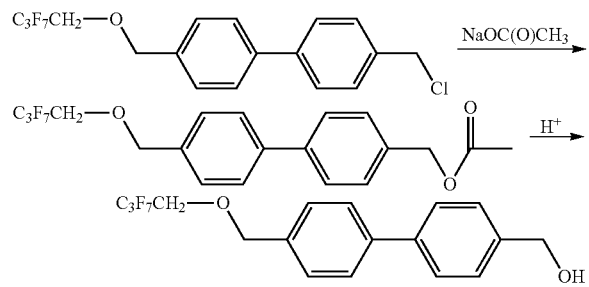

The product of Example 8 above (17.5 g) was stirred with 8.2 g NaOAc in 50 mL DMF at 80° C. for 4 hr. The reaction was quenched in water and the resulting sticky solid filtered, dissolved in methylene chloride, dried (MgSO$_4$), and stripped to 16.5 g of product, which showed IR absorption at 1740 cm$^{-1}$. This was combined with 0.4 g toluenesulfonic acid hydrate in 150 mL ethanol and stirred at reflux 20 hr. After stripping the solvent, the product, 4-(heptafluorobutoxymethyl)-4'-hydroxymethylbiphenyl, (10.9 g) was a solid, with broad OH absorption at 3345 cm$^{-1}$ and no IR absorption at 1740 cm$^{-1}$.

Example 10

Preparation of 4-((1H,1H,2H,2H-perfluoro-1-octyl)oxymethyl)-4'-chloromethylbiphenyl

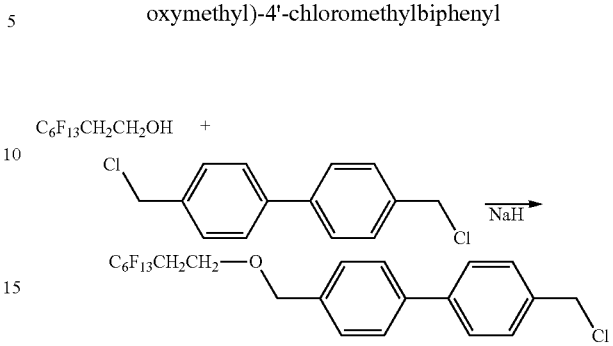

A boiling solution of 40.0 g (0.1 mol) 1H,1H,2H,2H-perfluoro-1-octanol and 25.1 g (0.1 mol) 4,4'-bis(chloromethyl)biphenyl in 150 mL THF was treated dropwise over 1 hr with 8.0 g 50% NaOH/water. The reaction was stopped at 2.5 hr and quenched in water and extracted with methylene chloride. This material (61.5 g) was a pale yellow solid with some liquid, C$_6$F$_{13}$C$_2$H$_4$OH by GLC. Trituration with hexane left 19.3 g solid, shown by GLC to be 55% dichloride plus two new products. The hexane was evaporated to 36.4 g. Trituration with perfluoromethylmorpholine left 26.4 g solid. GC/MS showed the major component (74%) to be the desired 4-((1H,1H,2H,2H-perfluoro-1-octyl)oxymethyl)-4'-chloromethylbiphenyl with the diether (4,4'-bis((1H,1H,2H,2H-perfluoro-1-octyl)oxymethyl)biphenyl as minor component.

Example 11

Preparation of 4-((1H,1H,2H,2H-perfluoro-1-octyl)oxymethyl)-4'-hydroxymethylbiphenyl and its acrylate

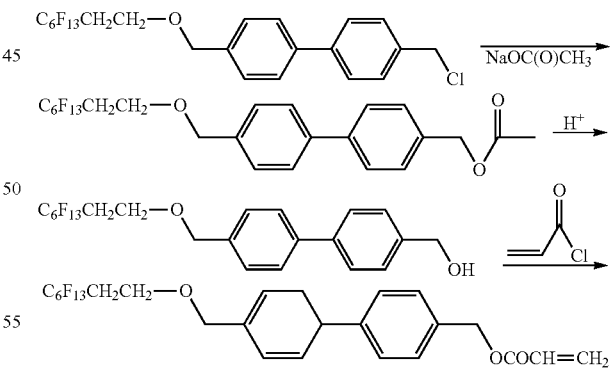

The product of Example 9 above (26.4 g) was stirred with 7.8 g NaOAc in 50 mL DMF at 80° C. for 18 hr. GLC showed complete conversion of the major component to a new material, with IR absorption at 1740 cm$^{-1}$. The mixture was quenched in water to yield a white solid, filtered and dried in methylene chloride over MgSO$_4$ and stripped to give 29.0 g. Of this, 19.6 g was extracted with 500 mL boiling perfluoro-N-methylmorpholine under magnetic stirring (thus dissolving essentially pure 4,4'-bis((1H,1H,2H,2H-perfluoro-1-octyl)oxymethylbiphenyl) and leaving a white solid. This was collected and heated into 400 mL hexane, filtered of a small amount of pale yellow solid, and the solution allowed to evaporate to give 12.1 g of 4-((1H,1H,2H,2H-perfluoro-1-octyl)oxymethyl)-4'-hydroxymethylbiphenyl, recrystallized from hexane to 8.4 g. Of this, 8.1 g (0.0145 mol) was dissolved in 100 mL methylene chloride and treated first with 1.5 g (0.0177 mol) acryloyl chloride and then dropwise with 2.3 g (0.0178 mol) diisopropylethylamine. Conversion to the acrylate was confirmed by GLC and IR spectrometry. The mixture treated with 5 mL MeOH and then washed with diluted HCl and then NaCl solution. The organic layer was dried over MgSO₄ and stripped. The residue was heated with hexane, filtered, and stripped to 5.8 g of 4-((1H,1H,2H,2H-perfluoro-1-octyl)oxymethyl)-4'-acryloxymethylbiphenyl, a waxy solid, with IR absorption at 1725 cm⁻¹. Of this, 5.4 g was dissolved in 21.6 g ethyl acetate containing 0.056 g VAZO 67 and the solution was purged with 1 L per minute (min) N₂ for 1 min in a polymerization bottle. This was heated in a water bath at 63° C. for 18 hr. The polymer was precipitated with methanol.

Example 12

Preparation of 4-(N-methylperfluorobutanesulfonamidomethyl)-4'-mercaptomethylbiphenyl

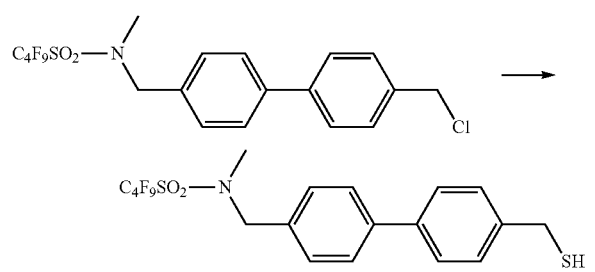

A mixture of 10.5 g (0.02 mol) of 4-(N-methylperfluorobutanesulfonamidomethyl)-4'-chloromethylbiphenyl, and 1.90 g (0.024 mol) thiourea in 100 mL methyl ethyl ketone was stirred and heated at reflux. The initial solution became cloudy and by 1 hr a white precipitate formed. The mixture was heated for 17 hr, cooled, and filtered. The product (8.2 g) was heated in 150 mL boiling ethanol under N₂ and treated with 8 g (0.1 mol) 50% NaOH and heated for 20 hr. The resulting hazy solution was cooled, treated with 20 mL 10% HCl, and poured into 200 mL water to give a white solid. This was taken up in methylene chloride, dried over MgSO₄, and stripped to 7.0 g of the desired product.

Example 13

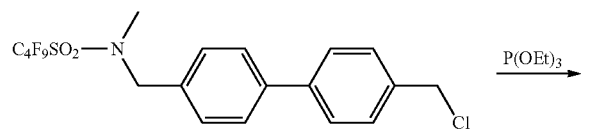

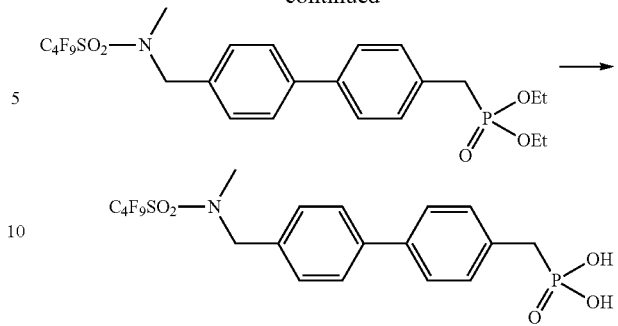

A mixture of 4-(N-methylperfluorobutanesulfonamidomethyl)-4'-chloromethylbiphenyl (0.03 mol, 15.8 g) and triethylphosphite (0.06 mol, 20 g) were heated to 140-150° C. for 24 hr. After cooling, excess triethylphosphite was removed in vacuum. Trimethylsilyl bromide (0.033 mol, 5.06 g) was added to a solution of 6.3 g of above crude product (0.01 mol) in 10 mL of dichloromethane. After stirring for 3 hr at room temperature, the mixture was concentrated under reduced pressure. Methanol (10 mL) was added and the mixture was stirred for 1 hr at room temperature. The solvent was evaporated and the product was dried to constant weight under vacuum.

Example 14

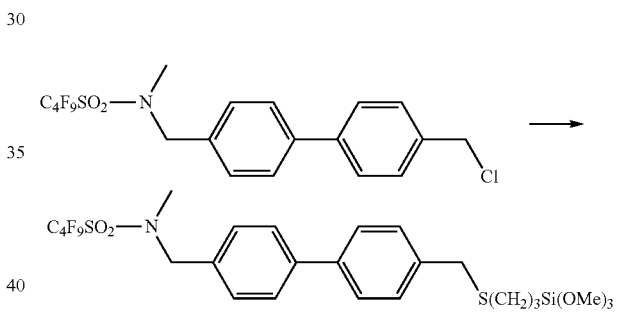

A mixture of 4-(N-methylperfluorobutanesulfonamidomethyl)-4'-chloromethylbiphenyl (0.005 mol, 2.64 g), HS(CH₂)₃Si(OMe)₃ (0.00525 mol, 1.03 g), K₂CO₃ (0.0075 mol, 1.03 g), and acetone was heated at 80° C. for 5 hr. After evaporation of the volatiles, ethyl acetate was added to re-dissolve the product. Then filtration was used to remove the salt. Evaporation of solvent gave the desired product.

Example 15

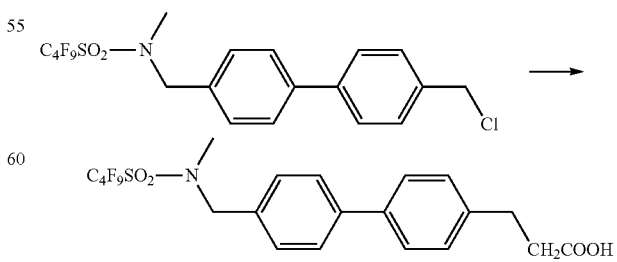

A 1-L single-necked flask was charged with 264 g (2.0 mol) dimethyl malonate and 432 g (2.0 mol) 25% sodium methoxide in methanol. The mixture was stripped on a rotary evaporator. About 200 mL toluene was added and the mixture was stripped for 20 hr to give NaCH(COOMe)$_2$ as a light tan powder, 305.9 g. A mixture of compound 4-(N-methylperfluorobutanesulfonamidomethyl)-4'-chloromethylbiphenyl (0.005 mol, 2.64 g), NaCH(COOMe)$_2$ (0.01 mol, 1.78 g) and ethanol (10 mL) was mixed and refluxed for 2 hr. Then 4 mL of KOH aqueous solution (10%) was added and refluxed for another 2 hr. Then 50 mL ethyl acetate was added, washed by water, dried by anhydrous magnesium sulfate. Evaporation of solvent by a rotary evaporator gave 2.4 g crude product.

General Procedure for Preparing Acrylates and Methacrylate Monomers

A mixture of 0.004 mol of alcohol and 0.0044 mol of acryloyl chloride or methacryloyl chloride, and 40 mL of 1,2-dimethoxyethane was charged into a flask with a magnetic stirrer. After the solution was cooled to 0° C., triethylamine (0.0044 mol, 0.45 g) was slowly added dropwise within 1 hr. After another hour at 0° C., the reaction was stopped. The solution was diluted by ethyl acetate, washed by water and sodium carbonate, and dried by anhydrous magnesium sulfate. Evaporation of solvent by a rotary evaporator gave the desired acrylate or methacrylate.

General Procedure for Preparing Urethane Methacrylate Monomers

A mixture of 0.0027 mol of alcohol and 0.00284 mol of isocyanatoethyl methacrylate, 20 mL ethyl acetate, and two drops of dibutyltin dilaurate were added to a polymerization bottle with a stirrer. At room temperature the solution was stirred for 2 days. The solvent was then evaporated, and the solid was redissolved in acetone and precipitated from water. The collected solid was dissolved in ethyl acetate and washed by water and sodium carbonate, and dried by anhydrous magnesium sulfate. Evaporation of solvent by a rotary evaporator gave the desired urethane methacrylate.

Examples 16-33

For each of Examples 16-33, 1 g of a monomer, prepared from one of the general procedure for preparing monomers described above, 0.02 g of VAZO 67, and 3 g of ethyl acetate were charged into a polymerization bottle and purged with nitrogen for 1 minute. Then the bottle was sealed and polymerization reaction was carried out at 55° C. for 48 hr. Methanol was used to precipitate the resulting polymer from ethyl acetate solution. The collected polymer was dried in vacuum oven at 60° C. for 24 hr.

Table 1 below summarizes the monomers used for each of Examples 16-33 as well as the DSC data (i.e., melting temperature, $T_m$, and glass transition temperature, $T_g$), water- and hexadecane-contact angles of polymers synthesized from indicated monomers.

The DSC data and contact angle data were obtained using the methods described above except that the polymer of Example 11 (prepared from the acrylate) was cured at 230° C. before contact angle measurements.

TABLE 1

| Example | Monomer Structure | $T_m$ | $T_g$ | Water Contact Angle Advancing | Water Contact Angle Receding | Hexadecane Contact Angle Advancing | Hexadecane Contact Angle Receding |
|---|---|---|---|---|---|---|---|
| 11 | 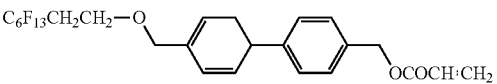 | | | 114 | 80 | 77 | 65 |
| 16 | 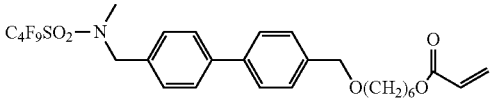 | 186 | 65 | 135 | 79 | 75 | 56 |
| 17 | 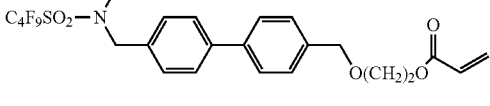 | 189 | 78 | 130 | 85 | 78 | 63 |
| 18 | 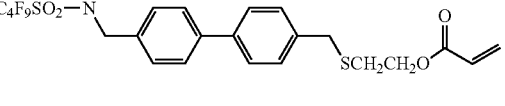 | 217 | | 127 | 91 | 75 | 65 |
| 19 | 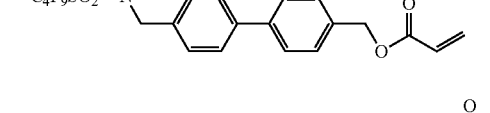 | 257 | 123 | 126 | 105 | 75 | 66 |
| 20 | 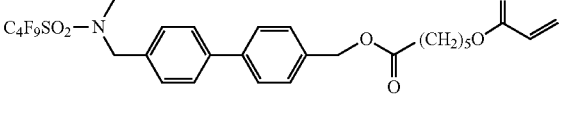 | 170 | | 124 | 93 | 77 | 66 |

TABLE 1-continued

| Example | Monomer Structure | $T_m$ | $T_g$ | Water Contact Angle Advancing | Water Contact Angle Receding | Hexadecane Contact Angle Advancing | Hexadecane Contact Angle Receding |
|---|---|---|---|---|---|---|---|
| 21 | $C_4F_9SO_2$-N(CH₃)-CH₂-C₆H₄-C₆H₄-CH₂-O-C(O)-(CH₂)-O-C(O)-CH=CH₂ | 243 | 91 | 127 | 105 | 78 | 67 |
| 22 | $C_4F_9SO_2$-N(CH₃)-CH₂-C₆H₄-C₆H₄-CH₂-O(CH₂)₂O-C(O)NH-CH₂CH₂-O-C(O)-C(CH₃)=CH₂ | 117 | 105 | 122 | 78 | 73 | 55 |
| 23 | $C_4F_9SO_2$-N(CH₃)-CH₂-C₆H₄-C₆H₄-CH₂-O(CH₂)₆O-C(O)NH-CH₂CH₂-O-C(O)-C(CH₃)=CH₂ | 186 | 56 | 122 | 88 | 74 | 59 |
| 24 | $C_4F_9SO_2$-N(CH₃)-CH₂-C₆H₄-C₆H₄-CH₂-O-C(O)NH-CH₂CH₂-O-C(O)-C(CH₃)=CH₂ | 239 | 82 | 123 | 93 | 74 | 67 |
| 25 | $C_4F_9SO_2$-N(CH₃)-CH₂-C₆H₄-C₆H₄-CH₂-O-C(O)-(CH₂)ₙO-C(O)NH-CH₂CH₂-O-C(O)-C(CH₃)=CH₂ | 139 | 48 | 121 | 96 | 75 | 64 |
| 26 | $C_4F_9SO_2$-N(CH₃)-CH₂-C₆H₄-C₆H₄-CH₂-SCH₂CH₂O-C(O)NH-CH₂CH₂-O-C(O)-C(CH₃)=CH₂ | 220 | 61 | 122 | 93 | 75 | 64 |
| 27 | $C_4F_9SO_2$-N(CH₃)-CH₂-C₆H₄-C₆H₄-CH₂-O(CH₂)₂O-C(O)-C(CH₃)=CH₂ | 166 | 61 | 121 | 92 | 72 | 61 |
| 28 | $C_4F_9SO_2$-N(CH₃)-CH₂-C₆H₄-C₆H₄-CH₂-O(CH₂)₆O-C(O)-C(CH₃)=CH₂ | 102 | 50 | 121 | 83 | 72 | 57 |
| 29 | $C_4F_9SO_2$-N(CH₃)-CH₂-C₆H₄-C₆H₄-CH₂-O-C(O)-C(CH₃)=CH₂ | 187 | | 118 | 92 | 69 | 61 |
| 30 | $C_4F_9SO_2$-N(CH₃)-CH₂-C₆H₄-C₆H₄-CH₂-SCH₂CH₂O-C(O)-C(CH₃)=CH₂ | 213 | 62 | 121 | 92 | 71 | 62 |
| 31 | $C_4F_9SO_2$-N(CH₃)-CH₂-C₆H₄-C₆H₄-CH₂-O-C(O)-(CH₂)₅-O-C(O)-C(CH₃)=CH₂ | 101 | | 122 | 98 | 76 | 63 |

TABLE 1-continued

| Example | Monomer Structure | $T_m$ | $T_g$ | Water Contact Angle Advancing | Water Contact Angle Receding | Hexadecane Contact Angle Advancing | Hexadecane Contact Angle Receding |
|---|---|---|---|---|---|---|---|
| 32 | C$_4$F$_9$SO$_2$—N(CH$_3$)—CH$_2$—[biphenyl]—CH$_2$—O—C(O)—CH$_2$O—C(O)—C(CH$_3$)=CH$_2$ | 205 | 80 | 120 | 91 | 71 | 62 |
| 33 | C$_4$F$_9$SO$_2$—N(CH$_3$)—CH$_2$—[biphenyl]—CH$_2$—O—C(O)—CH$_2$O—C(O)—NH—CH$_2$CH$_2$—O—C(O)—CH=CH$_2$ | 142 | | 125 | 99 | 73 | 63 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. An arylene-containing compound of formula (I):

Rf-L-CH$_2$—Ar—CH$_2$—Y-Q    (I)

wherein:
Ar is a phenylene or diphenylene;
Rf is a perfluoroalkyl having 3 to 6 carbon atoms or a group of formula $C_xF_{2x+1}(OC_yF_{2y})_aOC_pF_{2p}$—, wherein x is 1 to 4, y is 1 to 4, p is 1 to 4, and a is 0 to 20;
L is selected from —O—, —SO$_2$—, —CH$_2$—O—, —C$_2$H$_4$—O—, —C$_2$H$_4$—S—, and —SO$_2$—N(R$^1$)—;
R$^1$ is a C1-C4 alkyl;
Y is —O—, —S—, —NH—, —C(O)O—, —CH$_2$—C(O)O—, —CH$_2$—C(O)NH—, or together Y-Q is —P(O)(OR$^3$)$_2$, or —N$_3$;
wherein:
when Y is selected from —O—, —S—, or —NH—, then Q is selected from:
—H,
—C$_n$H$_{2n}$—OH,
—C(O)—C$_n$H$_{2n}$—OH,
—C(O)—O—C$_n$H$_{2n}$—OH,
—C(O)—C(R$^2$)=CH$_2$,
—C$_n$H$_{2n}$—O—C(O)—C(R$^2$)=CH$_2$,
—C(O)—C$_n$H$_{2n}$—O—C(O)—C(R$^2$)=CH$_2$,
—C(O)—NH—C$_n$H$_{2n}$—O—C(O)—C(R$^2$)=CH$_2$,
—C$_m$H$_{2m}$—O—C(O)—NH—C$_n$H$_{2n}$—O—C(O)—C(R$^2$)=CH$_2$,
—C(O)—C$_m$H$_{2m}$—O—C(O)—NH—C$_n$H$_{2n}$—O—C(O)—C(R$^2$)=CH$_2$, and
—(CH$_2$)$_3$Si(OR$^4$)$_3$;
or when Y is —C(O)O—, —CH$_2$—C(O)O—, or —CH$_2$—C(O)NH—, then Q is selected from:
—H,
—C$_n$H$_{2n}$—OH,
—C$_n$H$_{2n}$—O—C(O)—C(R$^2$)=CH$_2$, and
—C$_m$H$_{2m}$—O—C(O)—NH—C$_n$H$_{2n}$—O—C(O)—C(R$^2$)=CH$_2$;
R$^2$ is —H or —CH$_3$;
R$^3$ is —H, —CH$_3$, or —C$_2$H$_5$;
R$^4$ is a C1-C4 alkyl or —C(O)—CH$_3$;
b is an integer of 1 to 20;
m is an integer of 2 to 18; and
n is an integer of 2 to 18.

2. The compound of claim 1 wherein Y and Q are selected such that:
when Y is selected from —O— or —S—, then Q is selected from:
—H,
—C$_n$H$_{2n}$—OH,
—C(O)—C$_n$H$_{2n}$—OH,
—C(O)—O—C$_n$H$_{2n}$—OH,
—C(O)—C(R$^2$)=CH$_2$,
—C$_n$H$_{2n}$—O—C(O)—C(R$^2$)=CH$_2$,
—C(O)—C$_n$H$_{2n}$—O—C(O)—C(R$^2$)=CH$_2$,
—C(O)—NH—C$_n$H$_{2n}$—O—C(O)—C(R$^2$)=CH$_2$,
—C$_m$H$_{2m}$—O—C(O)—NH—C$_n$H$_{2n}$—O—C(O)—C(R$^2$)=CH$_2$,
—C(O)—C$_m$H$_{2m}$—O—C(O)—NH—C$_n$H$_{2n}$—O—C(O)—C(R$^2$)=CH$_2$, and
—(CH$_2$)$_3$Si(OR$^4$)$_3$;
or Y-Q is selected from:
—P(O)(OR$^3$)$_2$,
—N$_3$, and
—NH$_2$.

3. The compound of claim 2 wherein Y and Q are selected such that:
when Y is selected from —O— or —S—, then Q is selected from:
—H,
—C$_n$H$_{2n}$—OH,
—C(O)—C$_n$H$_{2n}$—OH,
—C(O)—O—C$_n$H$_{2n}$—OH,
—C(O)—C(R$^2$)=CH$_2$,
—C$_n$H$_{2n}$—O—C(O)—C(R$^2$)=CH$_2$,
—C(O)—C$_n$H$_{2n}$—O—C(O)—C(R$^2$)=CH$_2$,
—C(O)—NH—C$_n$H$_{2n}$—O—C(O)—C(R$^2$)=CH$_2$,
—C$_m$H$_{2m}$—O—C(O)—NH—C$_n$H$_{2n}$—O—C(O)—C(R$^2$)=CH$_2$,
—C(O)—C$_m$H$_{2m}$—O—C(O)—NH—C$_n$H$_{2n}$—O—C(O)—C(R$^2$)=CH$_2$, and
—(CH$_2$)$_3$Si(OR$^4$)$_3$;
or Y-Q is —P(O)(OR$^3$)$_2$.

4. The compound of claim 1 wherein Ar is a diphenylene.

5. The compound of claim 1 wherein Rf is of the formula $C_3F_7(OCF_2CF(CF_3))_aOCF(CF_3)-$, wherein a is 4 to 20.

6. The compound of claim 1 wherein L is selected from $-CH_2-O-$, $-C_2H_4-O-$, and $-SO_2-N(R^1)-$ wherein $R^1$ is a C1-C4 alkyl.

7. The compound of claim 6 wherein $R^1$ is $-CH_3$.

8. The compound of claim 1 wherein n is 2 to 12.

9. The compound of claim 8 wherein n is 2 to 6.

10. The compound of claim 1 wherein m is 2 to 12.

11. The compound of claim 10 wherein m is 2 to 6.

12. The compound of claim 1, wherein:
Ar is a diphenylene;
Rf is $-C_4F_9$ or $-C_6F_{13}$;
L is $-SO_2-N(R^1)-$ or $-C_2H_4-O-$;
Y and Q are selected such that:
when Y is selected from $-O-$ or $-S-$, then Q is selected from:
   $-H$,
   $-C(O)-C(R^2)=CH_2$,
   $-C_nH_{2n}-OH$,
   $-C_nH_{2n}-O-C(O)-C(R^2)=CH_2$,
   $-C(O)-C_nH_{2n}-OH$,
   $-C(O)-C_nH_{2n}-O-C(O)-C(R^2)=CH_2$, and
   $-C(O)-C_mH_{2m}-O-C(O)-NH-C_nH_{2n}-O-C(O)-C(R^2)=CH_2$;
$R^1$ is $-CH_3$;
$R^2$ is $-H$ or $-CH_3$;
m is an integer of 2 to 6; and
n is an integer of 2 to 6.

13. The compound of claim 12 of the formulas:

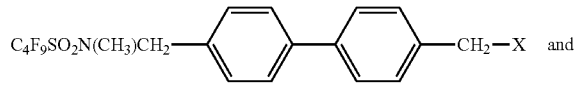

and

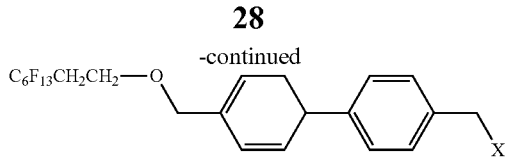

wherein X is selected from:
   $-SC_2H_4-O-C(O)-CH=CH_2$,
   $-O-C(O)-CH=CH_2$,
   $-O-C(O)-CH_2O-C(O)-CH=CH_2$,
   $-SC_2H_4-O-C(O)-C(CH_3)=CH_2$,
   $-O-C(O)-(CH_2)_5O-C(O)-C(CH_3)=CH_2$,
   $-O-C(O)-CH_2O-C(O)-C(CH_3)=CH_2$, and
   $-C(O)-CH_2O-C(O)-NH-C_2H_4-O-C(O)-CH=CH_2$.

14. The compound of claim 1, wherein
Y and Q are selected such that:
when Y is selected from $-O-$, $-S-$, or $-NH-$, then Q is selected from:
   $-C_nH_{2n}-O-C(O)-C(R^2)=CH_2$,
   $-C(O)-C_nH_{2n}-O-C(O)-C(R^2)=CH_2$,
   $-C(O)-NH-C_nH_{2n}-O-C(O)-C(R^2)=CH_2$,
   $-C_mH_{2m}-O-C(O)-NH-C_nH_{2n}-O-C(O)-C(R^2)=CH_2$, and
   $-C(O)-C_mH_{2m}-O-C(O)-NH-C_nH_{2n}-O-C(O)-C(R^2)=CH_2$;
or when Y is $-C(O)O-$, $-CH_2-C(O)O-$, or $-CH_2-C(O)NH-$, then Q is selected from:
   $-C_nH_{2n}-O-C(O)-C(R^2)=CH_2$, and
   $-C_mH_{2m}-O-C(O)-NH-C_nH_{2n}-O-C(O)-C(R^2)=CH_2$;
$R^2$ is $-H$ or $-CH_3$;
m is an integer of 2 to 18; and
n is an integer of 2 to 18.

15. A polymer prepared from a (meth)acrylate functionalized arylene-containing compound of claim 14.

* * * * *

UNITED STATES PATENT AND TRADEMARK OFFICE
CERTIFICATE OF CORRECTION

PATENT NO.         : 8,975,436 B2                                          Page 1 of 1
APPLICATION NO.    : 13/508080
DATED              : March 10, 2015
INVENTOR(S)        : Yu Yang It is certified that error appears in the above-identified patent and that said Letters Patent is hereby corrected as shown below:

In the specification

Column 10
Line 35, delete ""¯S" and insert -- —S --, therefor.

Line 37, delete ""¯S" and insert -- —S --, therefor.

Line 37, delete ""¯S—(CH$_2$)" and insert -- —S—(CH$_2$) --, therefor.

Line 39, delete ""¯O" and insert -- —O --, therefor.

Line 41, delete ""¯O" and insert -- —O --, therefor.

Line 42, delete ""¯S" and insert -- —S --, therefor.

Line 43, delete ""¯N$_3$" and insert -- —N$_3$ --, therefor.

Line 44, delete ""¯CH" and insert -- —CH --, therefor.

Signed and Sealed this
Twentieth Day of October, 2015

Michelle K. Lee
*Director of the United States Patent and Trademark Office*